(12) United States Patent
Houston et al.

(10) Patent No.: US 11,129,800 B2
(45) Date of Patent: Sep. 28, 2021

(54) PATCH COMPRISING POTASSIUM PERMANGANATE FOR THE TREATMENT OF SKIN DISORDER

(71) Applicant: NEEM BIOTECH LTD, Blaenau Gwent (GB)

(72) Inventors: David Houston, Cwmbran South Glamorgan (GB); Keith Harding, Cardiff South Glamorgan (GB); Charles Heard, Cardiff South Glamorgan (GB)

(73) Assignee: NEEM BIOTECH LTD, Blaenau Gwent (GB)

( * ) Notice: Subject to any disclaimer, the term of this patent is extended or adjusted under 35 U.S.C. 154(b) by 274 days.

(21) Appl. No.: 16/336,296

(22) PCT Filed: Sep. 21, 2017

(86) PCT No.: PCT/GB2017/052816
§ 371 (c)(1),
(2) Date: Mar. 25, 2019

(87) PCT Pub. No.: WO2018/055376
PCT Pub. Date: Mar. 29, 2018

(65) Prior Publication Data
US 2019/0224133 A1   Jul. 25, 2019

(30) Foreign Application Priority Data
Sep. 23, 2016   (GB) .................................... 1616223

(51) Int. Cl.
| | | |
|---|---|---|
| *A61K 9/70* | (2006.01) | |
| *A61P 17/10* | (2006.01) | |
| *A61P 31/22* | (2006.01) | |
| *A61P 17/02* | (2006.01) | |
| *A61P 31/04* | (2006.01) | |
| *A61P 31/10* | (2006.01) | |
| *A61K 9/00* | (2006.01) | |
| *A61K 33/32* | (2006.01) | |
| *A61K 47/34* | (2017.01) | |
| *A61P 17/00* | (2006.01) | |
| *A61P 31/00* | (2006.01) | |

(52) U.S. Cl.
CPC .......... *A61K 9/7007* (2013.01); *A61K 9/0014* (2013.01); *A61K 33/32* (2013.01); *A61P 17/02* (2018.01); *A61P 17/10* (2018.01); *A61P 31/04* (2018.01); *A61P 31/10* (2018.01); *A61P 31/22* (2018.01)

(58) Field of Classification Search
CPC .... A61K 33/32; A61K 9/0014; A61K 9/7007; A61P 17/02; A61P 17/10; A61P 31/04; A61P 31/10; A61P 31/22
See application file for complete search history.

(56) References Cited

U.S. PATENT DOCUMENTS 5,792,090 A   8/1998   Ladin

FOREIGN PATENT DOCUMENTS

| GB | 1412970 A | 11/1975 |
|---|---|---|
| WO | WO 2007/137732 A2 | 12/2007 |
| WO | WO 2016/131096 A1 | 8/2016 |

OTHER PUBLICATIONS

European Patent Office (EPO), International Search Report, Form PCT/ISA/210 for International Application No. PCT/GB2017/052816 (3 pages).
European Patent Office (EPO), Written Opinion of the International Searching Authority, Form PCT/ISA/237 for International Applicaiton No. PCT/GB2017/052816 (5 pages).

*Primary Examiner* — Jeffrey T. Palenik
(74) *Attorney, Agent, or Firm* — Pauley Erickson & Swanson (57) ABSTRACT

The invention relates to medical treatment patch, ideally for applying topically, that permits the targeted, sustained and controlled release of potassium $KMnO_4$; and a method of treating a skin disorder comprising applying said patch.

20 Claims, 10 Drawing Sheets

PATCH COMPRISING POTASSIUM PERMANGANATE FOR THE TREATMENT OF SKIN DISORDER

FIELD OF THE INVENTION

The invention relates to medical treatment patch, ideally for applying topically, that permits the targeted, sustained and controlled release of potassium $KMnO_4$; and a method of treating a skin disorder comprising applying said patch.

BACKGROUND OF THE INVENTION

There is enormous pressure on healthcare systems to decrease the use of systemic antibiotics and also long-term use of topical antimicrobial treatments given the increasing incidence of antimicrobial resistance.

Potassium permanganate ($KMnO_4$) solution has long been recognised as an effective microbicide and is commonly used to treat a variety of dermatological conditions, such as fungal infections of the legs and feet and chronic wounds characterised by colonization of antimicrobial resistant bacteria (i.e. Ciprofloxacin resistant *Pseudomonas aeruginosa*, MRSA). The microbicide properties are attributed to its strong oxidising properties. It can also exhibit astringent properties which is why it has utility in the treatment of weeping or blistering conditions such as acute infected eczema and leg ulcers. Potassium permanganate is thus a very effective treatment for those patients who have heavily exuding, infected wounds (particularly *Pseudomonas*) and also infection associated skin conditions e.g. varicose eczema. For safety reasons, not allowing its use has implications from a clinical perspective: there is no alternative treatment for these patients and without it there is an increase in dressing use, antibiotic treatments, nurse time and misery for the patients.

Potassium permanganate therapy is typically undertaken by first diluting tablets of potassium permanganate in a defined volume of water. The solution is then administered by submerging the area to be treated in a container of $KMnO_4$ for a period of up to 30 minutes. This practice, though effective, has many disadvantages.

The current wash system effectiveness is due to the highly oxidative nature of $KMnO_4$ (Purple, $Mn^{7+}$) which is reduced to brown manganese dioxide ($Mn^{4+}$). Bacteria cannot become resistant to this type of antimicrobial oxidation. As a side effect of this reaction and the non-specific delivery of the drug, healthy skin and healing epidermis is unavoidably damaged. The brown $Mn^{4+}$ also precipitates out of solution and causing the staining of surrounding tissue, floors, bedding and towels. This process also takes a great deal of time and space to deliver, with a total time of preparation application and cleaning taking up to an hour to complete.

Additionally, the lack of targeted delivery can lead to hazardous side effects such as irritation to the eyes and mucous membranes. Moreover, due to the nonspecific oxidation of proteins/carbohydrates by $KMnO_4$ it is imperative that the localised concentration of $KMnO_4$ does not exceed a level that is toxic to cells or above the accepted concentration of $KMnO_4$ (63 mM) which can otherwise lead to potentially dangerous chemical burns.

This relatively crude preparation method and handling is reflected by the recent issuance of stage one warning for the use of potassium permanganate tablets within the community, due to the fact that "in the past 3.5 years 43 patients who ingested these and a large number (>1000) of incidents when improper dissolution or use led to hospitalisation".

Further, there has been a safety bulletin sent out prohibiting all community nurses filling potassium permanganate containers due to reported back injuries; leading to the prevention of potassium permanganate soaks.

We herein disclose a silicone treatment patch that permits the targeted, sustained and controlled release of potassium $KMnO_4$. Fabricated from a specific liquid silicone matrix, the patch contains dispersed micro particulate $KMnO_4$ which undergoes dissolution leading to its release in a controlled and sustained manner directly into the treatment site where it exerts its potent microbiocidal action. We have determined that over a 30 min application time the dose released is bioequivalent to that used in the current treatment. By controlling crystal size, it has been possible to develop a patch having standardised controlled release of $KMnO_4$ per surface area of silicone that does not exceed a localised concentration greater than 63 mM upon dissolution.

In addition, we have found that our patch only releases permanganate upon contact of the patch with an aqueous environment (for example, wound exudate). This is advantageous in certain treatment contexts as it ensures a targeted delivery to specific treatment areas. For example, in chronic wounds the exudate level and surface moisture can vary greatly, due to level of infection and level of healing. This not only varies between wounds but also varies across a single wound. A wound with a high bio burden exudes at much greater rate than one with a lower level of infection. Therefore, the more infected the greater the moisture level of the wound—the corollary of this is that as healing progresses the wound exudes progressively less exudate, particularly at the periphery. Thus, the release of permanganate is inherently tailored to deliver a requisite amount of permanganate to those areas in greatest need of treatment whilst the areas of the wound that are healing/normal are drier/dry and therefore not exposed to permanganate, or increased amounts thereof, so protecting the healing process from the adverse toxicity associated with the current treatment regimen. The inference here is that release from the matrix is to an extent, self-limiting.

Furthermore, the specific polydimethylsiloxane and curing process of the silicone patch is done in a way that creates innate adhesiveness whereby the patch will remain in place on a wound, but will not pull away parts of the wound upon removal. These properties are considered beneficial in retaining the patch at the point of application.

STATEMENTS OF INVENTION

According to a first aspect of the invention there is provided a patch for applying to the skin of a subject comprising medical grade silicone wherein said silicone has a shore hardness between 5-60A and dispersed therein potassium permanganate particles.

Notably, upon application of the patch to the skin the permanganate is controllably released from the patch in a moisture dependent manner.

Medical grade silicone is a term well known to those skilled in the art and is routinely used to classify silicone with biocompatible properties that allow it to be safely used in contact with living tissue. A biocompatible material is a material that is safe to use as it does not cause toxicity or chemical reactivity with the body such as an adverse immune response in the patient's body. Medical grade silicone is typically manufactured in carefully controlled environments to prevent contamination with other materials that could compromise the biocompatibility of the final product.

As is known to those skilled in the art, silicones are a group of synthetic polymers used in many medical devices due to their flexibility, heat resistance, and low toxicity and chemical reactivity. Silicones vary in their physical and chemical properties and in their suitability for medical use, according to their composition and structure. In this regard, it has been found that certain medical grade silicones, specifically those having a specific shore hardness have preferable features of flexibility, mouldability and texture appropriate for use as a patch when applied to the skin surface. Shore hardness is measure of the hardness of materials, specifically providing a measure of the resistance of plastics toward indentation and provide an empirical hardness value that does not necessarily correlate well to other properties or fundamental characteristics. As is known to those skilled in the art, shore hardness is typically measured using a Durometer, and consequently is also known as 'Durometer hardness'. There are several scales of durometer, used for materials with different properties. The two most common scales, using slightly different measurement systems, are the ASTM D2240 type A and type D scales. The A scale is for softer plastics, while the D scale is for harder ones.

As will be appreciated by those skilled in the art silicone can be in the form of liquid rubber or, following curing, solid rubber of varying degrees of hardness. In the context of the present invention, said silicone is therefore post-cure rubber wherein said shore hardness is a measure of the hardness of the silicone following the curing process.

Therefore, specifically, the patch as disclosed herein has a shore hardness between 5-60A, including every 0.1A there between. More preferably, said silicone has a shore hardness between 5-40A. Yet more preferably said silicone has a shore hardness between 10-40A. Yet more preferably still, said silicone has a shore hardness between 15-40A. Most ideally said silicone has a shore hardness selected from the group comprising: 10A, 11A, 12A, 13A, 14A, 15A, 16A, 17A, 18A, 18A, 19A, 20A, 21A, 22A, 23A, 24A, 25A, 26A, 27A, 28A, 29A, 30A, 31A, 32A, 33A, 34A, 35A, 36A, 37A, 38A, 39A, 40A and every 0.1A there between.

Examples of medical grade silicone include, but are not limited to, medical grade range for limited exposure, prolonged exposure and permanent contact with a shore hardness specification of 5-90A these silicones can be obtained from primasil silicones limited. NuSil Technology LLC, Dow Corning, Polymer systems technology limited, SIMTEC Silicone Parts LLC, Advanced polymers Ltd, AB specialty silicones.

Reference herein to potassium permanganate refers to the well-known inorganic compound with the chemical formula $KMnO_4$. It is typically a crystalline salt consisting of $K^+$ and $MnO_4^-$ ions. Also, formerly known as potash or Condy's crystals, it is a strong oxidizing agent and its crystals readily dissolves in water to give intensely pink or purple solutions. Accordingly, said potassium permanganate particles are in crystalline form dispersed throughout the silicone patch.

In a preferred embodiment of the invention, said permanganate particles have an average diameter between 1 nm-60 µm and every 0.1 µm there between. More preferably, said permanganate particles have an average diameter between 1-50 µm and every 0.1 µm there between. More preferably said permanganate particles have an average diameter between 5-35 µm. More preferably still said permanganate particles have an average diameter between 10-35 µm. Most ideally, said permanganate particles have an average diameter selected from the group comprising: 10 µm, 11 µm, 12 µm, 13 µm, 14 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, 30 µm, 31 µm, 32 µm, 33 µm, 34 µm, 35 µm, and every 0.1 µm there between.

The size of particles is important; a collection of large particles will yield the same concentration of $KMnO_4$ per $cm^2$ compared to a collection of small particles. However, with large particles the localised concentration of a solution is very high and thus detrimental/toxic to viable cells.

In addition to its physical properties, it has also been unexpectedly found that the silicone shore hardness in combination with the particle size of the permanganate particles dispersed therein correlates with the rate of release and dispersion profile of the permanganate from the patch, with the specific shore hardness disclosed herein leading to a controlled and linear release of permanganate from same to the surface of the skin to which it is applied.

As taught herein, and according to some recommended clinical guidelines, the localised concentration of $KMnO_4$ does not exceed a level that is toxic to cells or above the concentration of $KMnO_4$ (63 mM).

To achieve this dispersion, various loading (weight %) concentrations of permanganate crystals of defined particle size were added to silicone and homogenously mixed to provide a homogenous silicone pre-cured liquid silicone rubber, which is cured conventionally to produce a cured silicone rubber. The term '% by weight' is given its conventional meaning in the art and is construed as the proportion of solute (i.e. permanganate) in the overall solution (silicone and permanganate) represented as a percentage figure e.g. 1 g of permanganate in a 1 g solution of silicone represent 50% wt. As will be appreciated by those skilled in the art, in order to effect equal and uniform release of the permanganate, a homogenous dispersal of particles in the silicone is required.

Therefore, in yet a further preferred embodiment of the invention said permanganate particles are present in an amount between 5-75% by weight of the silicone patch and every 1% interval there between. More preferably, said permanganate particles are present in amount between 10-60% by weight, and more preferably still between 10-50% by weight. Most ideally said particles are present in an amount selected from the group comprising: 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, and every 0.1% there between.

In the context of the invention a slow release patch typically has a particle weight % of 10-25, including all 1 unit intervals there between and ideally 10%.

In the context of the invention a medium release patch typically has a particle weight % of 30-40, including all 1 unit intervals there between and ideally 35%.

In the context of the invention a fast release patch typically has a particle weight % of 45-50, including all 1 unit intervals there between and ideally 48%.

We have discovered that the level of exposure of the skin to permanganate and the release rate from our silicone patch can be carefully controlled by varying the particle size of potassium permanganate and its loading concentration. This property is advantageous, as the patch can be tailored accordingly to deliver the requisite rate and concentration of potassium permanganate release, which as will be appreciated by those skilled in the art, can vary according to the nature of the therapeutic need.

Figure 4:
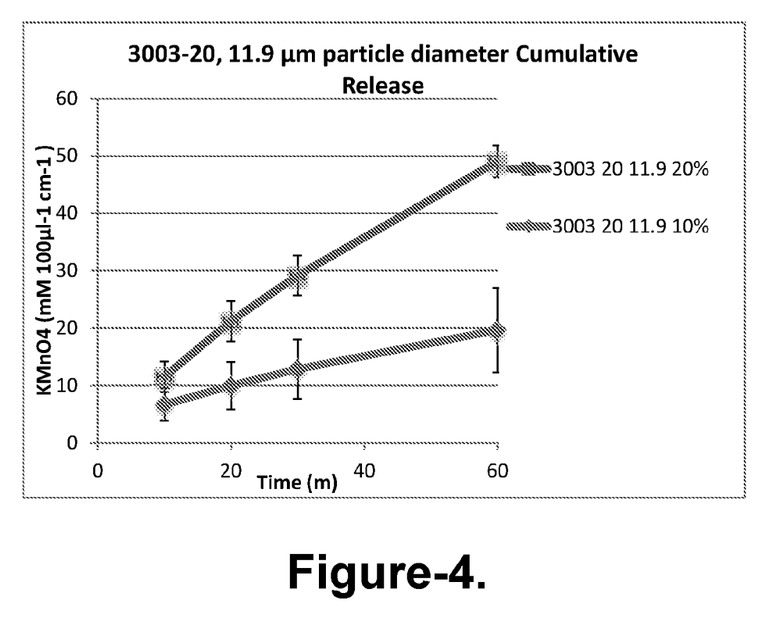
FIG. 4. The cumulative release of jet milled KMnO$_4$ particles having a diameter of 11.9 μm from silicone patches 3003-20 (shore hardness 20A) with 10% and 20% loading (N=3, ±SD). (note 3003 20 50% non-cure)
Figure 5:
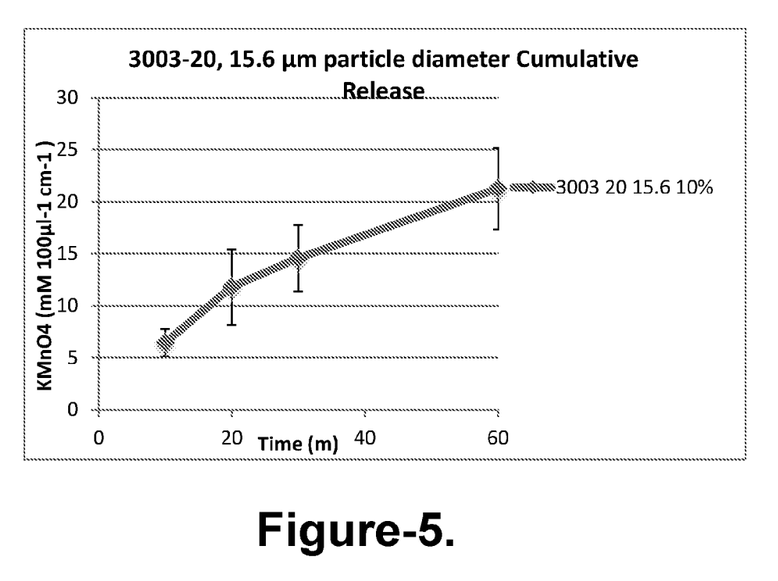
FIG. 5. The cumulative release of jet milled KMnO$_4$ particles having a diameter of 15.6 μm from silicone patches 3003-20 (shore hardness 20A) with 10% loading (N=3, ±SD). (note 3003 20 μm 20% 50% non-cure)

Accordingly, in a further preferred embodiment said silicone has a shore hardness of about 20A, said potassium permanganate dispersed therein is of a particle size of about 12 μm and at a concentration of about 20% by weight. As disclosed in FIG. 4, in this manner a slower and prolonged controlled release of permanganate can be achieved thus providing a flexible patch and slow-release/long duration patch.

Figure 6:
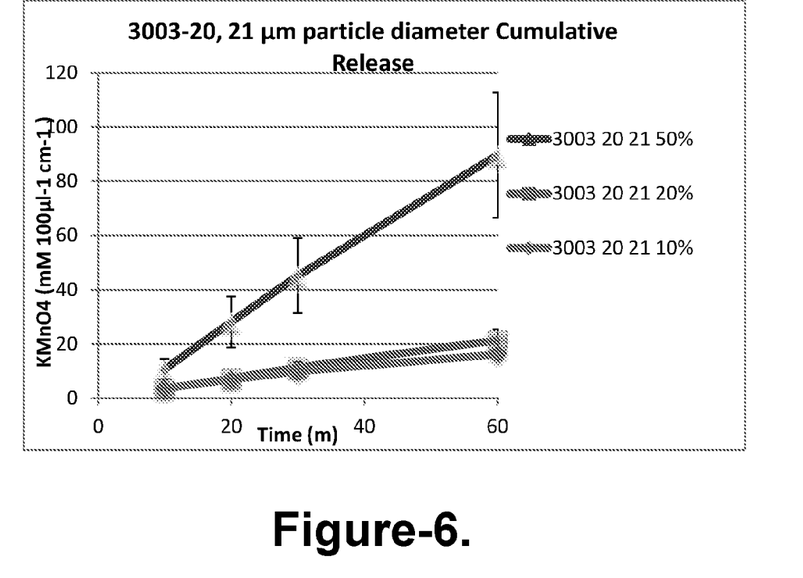
FIG. 6. The cumulative release of jet milled KMnO$_4$ particles having a diameter of 21 μm from silicone patches 3003-20 (shore hardness 20A) with 10%, 20% and 50% loading (N=3, ±SD)

Alternatively, said silicone has a shore hardness of an amount about 30A, said potassium permanganate dispersed therein is of a particle size of about 20 μm and at a concentration of about 50% by weight. As disclosed in FIG. 6, in this manner a slower controlled release of permanganate can be achieved thus providing a less flexible patch and slow-release/long duration patch.

Figure 7:
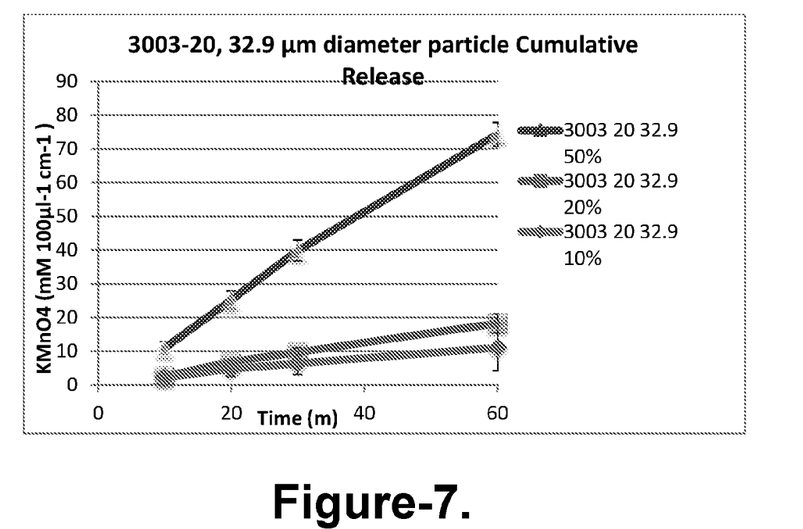
FIG. 7. The cumulative release of jet milled KMnO$_4$ particles having a diameter of 32.9 μm from silicone patches 3003-20 (shore hardness 20A) with 10%, 20% and 50% loading (N=3, ±SD)

Alternatively still, said silicone has a shore hardness of an amount about 40A, said potassium permanganate dispersed therein is of a particle size of about 33 μm and at a concentration of about 50% by weight. As disclosed in FIG. 7, in this manner a slower controlled release of permanganate can be achieved thus providing a substantially rigid patch and slow-release/long duration patch.

Thus, whether a flexible (20A), moderate (30A) or less (40A) flexible patch is desired one can tailor the formulation of the potassium permanganate in the patch to provide a slow acting patch.

Reference herein to "about" includes reference to plus or minus 10% of the recited integer value, or more preferably, plus or minus 5% of the recited integer value or more preferably still, plus or minus 1% of the recited integer value.

In yet a further preferred embodiment, said silicone has a shore hardness of an amount about 25A, said potassium permanganate dispersed therein is of a particle size of about 33 μm and at a concentration of about 50% by weight. As disclosed in FIG. 3, in this manner a rapid controlled release of permanganate can be achieved thus providing a flexible patch and rapid-release/short duration treatment patch.

Figure 8:
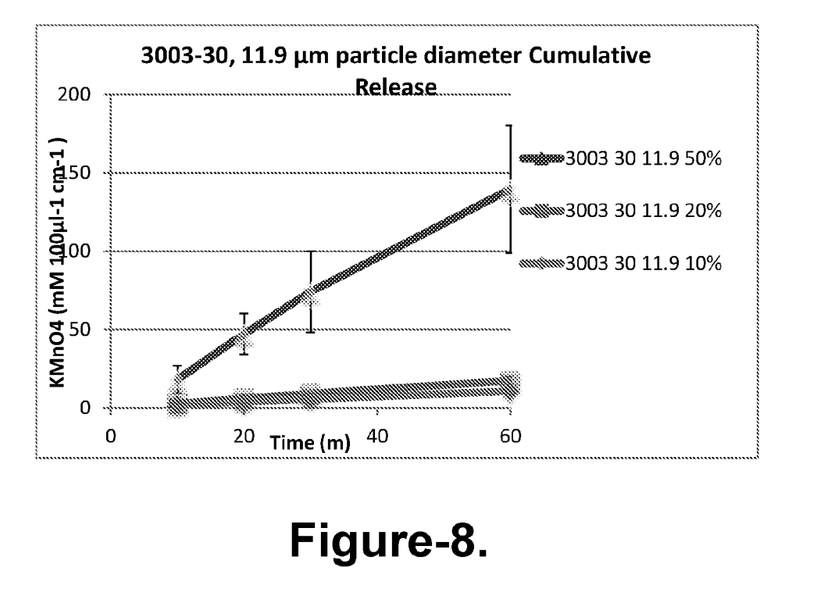
FIG. 8. The cumulative release of jet milled KMnO$_4$ particles having a diameter of 11.9 μm from silicone patches 3003-30 (shore hardness 30A) with 10%, 20% and 50% loading (N=3, ±SD)
Figure 9:
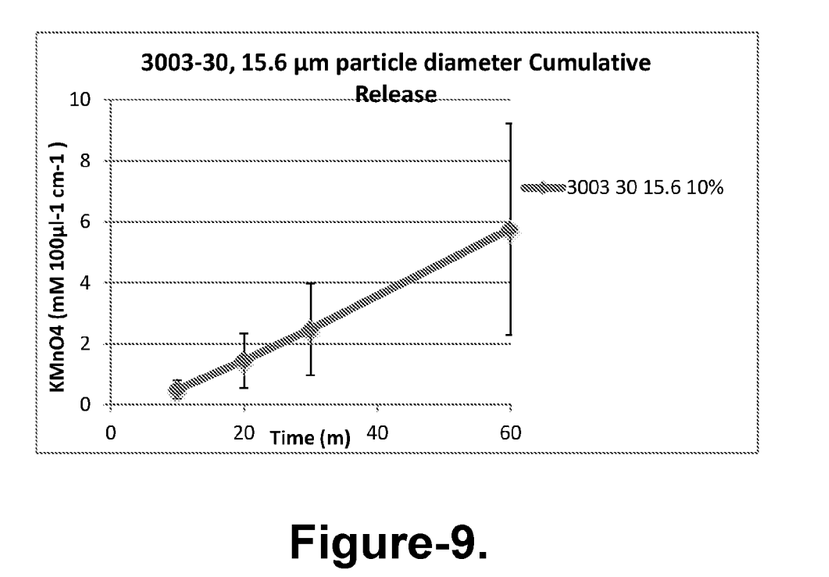
FIG. 9. The cumulative release of jet milled KMnO$_4$ particles having a diameter of 15.6 μm from silicone patches 3003-30 (shore hardness 30A) with 10% loading (N=3, ±SD). (note 3003 20 μm 20% 50% non-cure)
Figure 10:
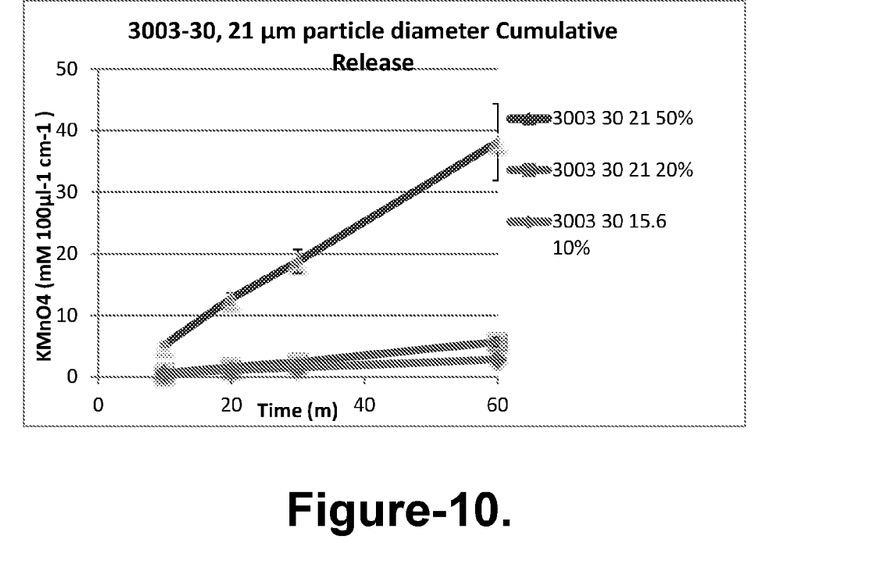
FIG. 10. The cumulative release of jet milled KMnO$_4$ particles having a diameter of 21 μm from silicone patches 3003-30 (shore hardness 30A) with 10%, 20% and 50% loading (N=3, ±SD)
Figure 11:
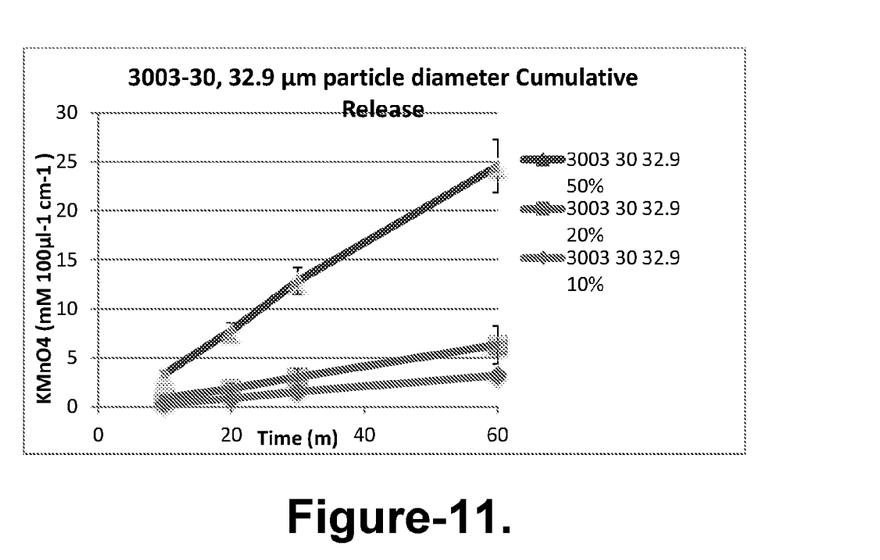
FIG. 11. The cumulative release of jet milled KMnO$_4$ particles having a diameter of 32.9 μm from silicone patches 3003-30 (shore hardness 30A) with 10%, 20% and 50% loading (N=3, ±SD)

Alternatively, said silicone has a shore hardness of an amount about 38A, said potassium permanganate dispersed therein is of a particle size of about 12 μm and at a concentration of about 50% by weight. As disclosed in FIG. 8, in this manner a rapid controlled release of permanganate can be achieved thus providing a less flexible patch and rapid-release/short duration treatment patch.

Thus, whether a more (25A) or less (38A) flexible patch is desired, one can tailor the formulation of the potassium permanganate in the patch to provide a fast-acting patch.

Additionally, it has been found that the patch as disclosed herein only releases potassium permanganate when there is a sufficient level of moisture on the surface to which the patch is applied e.g. such as in contact with a weeping wound. This feature of environmental influence upon permanganate release from the patch is advantageous as it means the delivery of potassium permanganate from the patch is self-regulating as it only administers potassium permanganate to a wound that is not healed, and further the levels correlate with the degree of moisture. Thus, the release of potassium permanganate is inherently tailored to deliver a requisite amount of potassium permanganate to those areas in greatest need of treatment whilst the areas of the wound that are healing/normal are drier/dry and therefore not exposed to potassium permanganate, or increased amounts thereof, and so protecting the healing process from adverse toxicity potentially associated with the treatment.

Additionally, this feature also ensures that elution of the active compound only occurs typically once applied to a wound leading to improved handling (such as for healthcare professionals or manufacturing staff) as risk of release other than to the desired treatment site is minimized. Further, the manufactured patch has greater stability facilitating storage and transportation.

According to a second aspect of the invention there is disclosed a method for treating a skin disorder characterized by increased skin surface moisture, said method comprising the step of applying the patch as disclosed herein to the surface of the skin to be treated whereupon contact with said skin surface moisture, potassium permanganate is released from the patch.

In a preferred method of the invention said patch is selected having regard to the preferred treatment time and so a slow-release/long duration patch of selected silicone flexibility may be chosen or a rapid-release/short duration treatment patch of selected silicone flexibility may be chosen.

In a preferred embodiment of the invention, said skin disorder includes, but is not limited to, wounds; chronic wounds; acute wounds; incisions; lacerations; abrasions; avulsions; punctures; thermal or chemical burns; bites and stings; ulcers; eczema; viral, fungal, or bacterial skin infections; acne; bowens disease; squamous cell carcinoma; contact dermatitis; Dystrophic epidermolysis bullosa; fungal infections of nails; herpes simplex; psoriasis; Pyoderma gangrenosum; and shingles.

Treatment herein includes reference to human or veterinary use.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

The Invention will now be described by way of example only with reference to the Examples below and to the following Figures wherein:

3003-10

3003-20

3003-30

3003-40

APPLICATION OF PATCH

FIG. 16a-c. Application of permanganate impregnated patch for thirty min on dry skin with no release. [A] skin prior to application. [B] patch applied. [C] skin unstained post 30 min application; and FIG. 17a-c. Application of permanganate impregnated patch for thirty min on wetted skin with release. [A] skin prior to application. [B] patch applied. [C] skin stained post 30 min application.

Table 1. Tested shore hardness of the different patches when loaded with varying particle sizes and concentrations of permanganate.

Materials and Methods

Potassium permanganate was purchased from Fischer Scientific. Medical grade Silicone (denoted 3003) part A and Part B was purchased from Primasil silicones limited according to defined shore hardness. When preparing the silicone patches, as will be appreciated, the overall hardness of the eventual cured silicone is influenced by loading with the permanganate (and dependent upon the loading concentration and particle size. Consequently, the shore hardness post cure when loaded was measured and shown in Table 1.

KMnO4 Particles

Potassium permanganate particles were created via two separate methods: i) ball milling and manual sieving; and ii) jet milling and mechanical sieving. Ball milling and manual sieving is a quick and low-cost method for producing particles within broad size acceptance. Conversely, jet milled particles requires use of specific equipment leading to extremely precise and defined particulate size; these particles were also been measured for the d50 particle size prior to use.

Ball Milling

Potassium permanganate crystals (10 g) were placed inside a steel ball mill containing 100 steel balls (1 cm) and the container was two thirds filled with cyclohexane (~200 mL). This was sealed and rotated at 200 rpm for 24 hrs. Following this the particles were poured through sieve stacks in excess cyclohexane and continuous rocking over 5 hours, excess cyclohexane was discarded as needed. The sieve stacks were allowed to dry within the fume cupboard (48 hrs), after which each sieve was emptied into a container and separately gently ground with pestle and mortar to break up any caking. Each sample of particles was placed back into their respective sieves, the sieves were stacked and then manually rocked and agitated via repeated hitting of the stack for a period of two hours. Each section was then removed and placed into a separate beaker and excess cyclohexane was added to each sample to make a slurry. Each slurry was poured back into the respective sieve, starting at the lowest particle size then stacking each subsequent sieve on top, each time washing through with excess cyclohexane. The stack was then left to dry within the fume cupboard for 48 hr. The process of drying, sieving, pestle and mortaring, slurry sieving then drying was repeated three times. After which the particles were removed from each sieve with the cake being gently broken by pestle and mortar followed by a dry sieve in stacks (2 hrs). The particles were removed from each sieve and stored in dry sealed containers, occluded from light and maintained at room temperature (21° C.).

Jet Milling

Potassium permanganate crystals were jet milled by Hosakawa micron into four different particles sizes: d50 11.9 μm, total weight 294 gm trial no 51461/run 3, total weight D50 15.6 μm total weight 75 gm, trial no 51461/run 1, D50 21 µm total weight 282 gm trial no 51461/run 6 and D50 32.9 µm total weight 279 gm trial no 51461/run 9

Patch Manufacture

Medical Grade 1.5 grams of part a and part b liquid silicone rubber were weighed out into a sterile petri dishes, these were manually mixed with a spatula after which the weighed particles were added to the silicone (50%=3 gm, 20%=0.75 gm, 10%=0.33 gm of particles). These were manually mixed using a spatula for 30 mins to ensure homogeneity after which the silicone was hand spread over the lid of a petri dish and left to gently rock for 3 hours to enable settling and flattening. Each patch was 8 cm in diameter having a thickness of 0.5 mm. These were then cured for 24 hr at 75° C. Patches were removed from the oven and left to cool then manually removed from the petri dish. Each patch was made three times; if curing did not occur patches were made 10 times and left at 75° C. for 1 week. In all instances if the patch was not cured after 24 hours it was found to never cured over 1 week or at increased temp (up to 120° C.).

Release Data

Patches were removed from the petri dish and inverted to ensure similar physical properties of the patch surface, i.e. completely flat, smooth and shiny.

The delivery section (lid) of a Franz diffusion cell was placed on each patch and the flanges were pre-greased with silicone gel to ensure a complete sea. The patch and Franz diffusion cell lid was securely clamped into position. 1 mL of $dH_2O$ was pipetted into the delivery lid of the FDC and fully collected after 10, 20 30 and 60 min. Upon collection, the sample was mixed manually three times with a 1 mL pipette before removal for analyses.

Analysis

Analysis was conducted via a UV Vis machine at 256 ηm using 1 mL plastic cuvettes, when the concentration was too high the sample was diluted in $dH_2O$.

Results

Release from Silicone 3003-10

Figure 1:
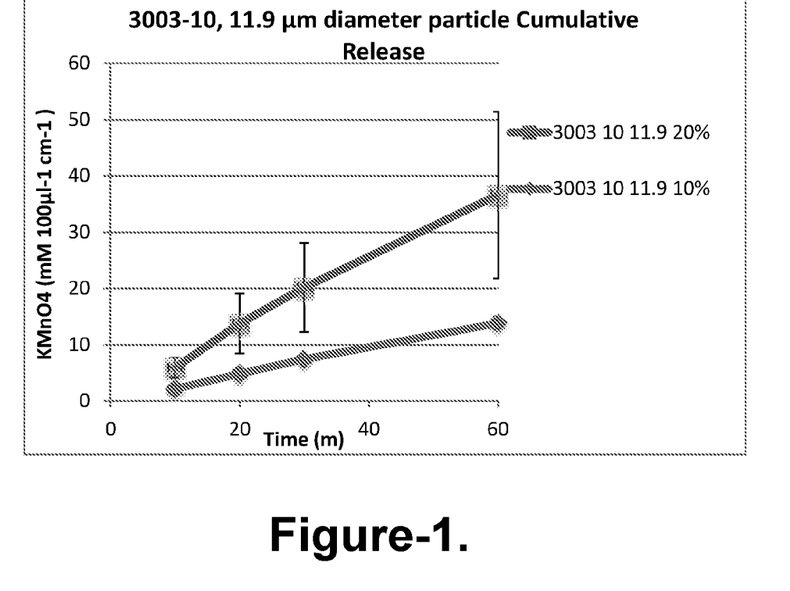
FIG. 1. The cumulative release of jet milled KMnO$_4$ particles having a diameter of 11.9 μm from silicone patches 3003-10 (shore hardness 10A) with 10% and 20% loading (N=3, ±SD). (Note 3003-10 11.9 μm 50% non-cure)
Figure 2:
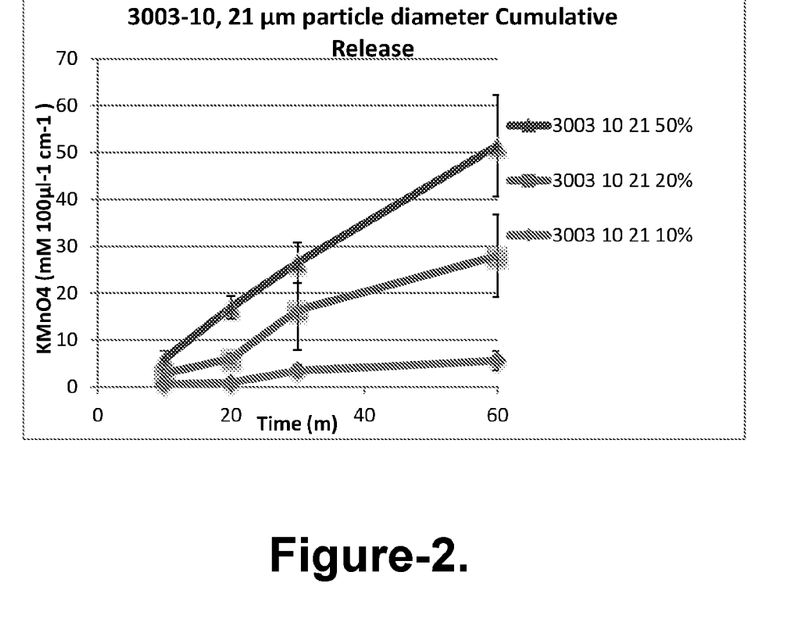
FIG. 2. The cumulative release of jet milled KMnO$_4$ particles having a diameter 21 μm from silicone patches 3003-10 (shore hardness 10A) with 10%, 20% and 50% loading (N=3, ±SD)
Figure 3:
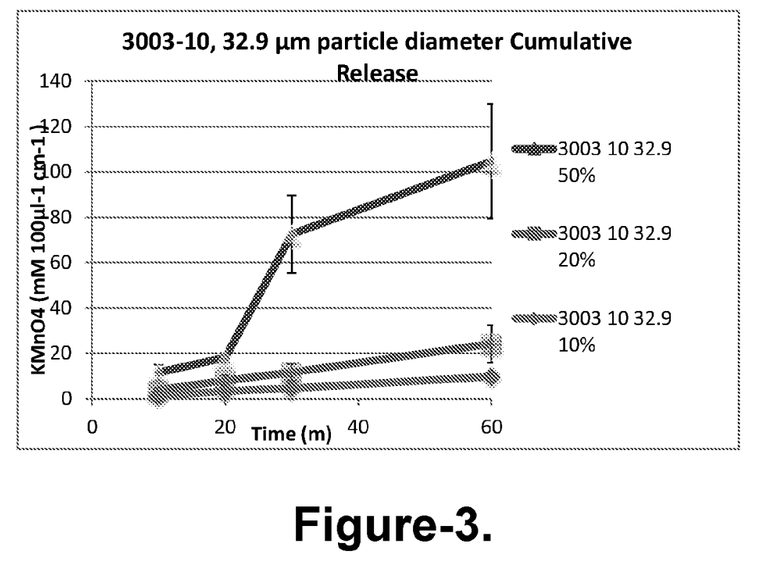
FIG. 3. The cumulative release of jet milled KMnO$_4$ particles having a diameter of 32.9 μm from silicone patches 3003 10 (shore hardness 10A) with 10%, 20% and 50% loading (N=3, ±SD)

Silicone 3003-10 release profiles in FIGS. 1, 2, and 3 show, in general, the trends: i) the smaller the particle size the greater the release; ii) the larger the concentration of loading the greater the release; and iii) in most cases a linear release profile over 1 hr.

When comparing the total release of 10% and 20% loading across all three particle sizes, in each case and at each time point the greater the loading the greater the release and the smaller the particle the greater the release. The only times this is not true is when comparing 50% loading of particle size 21 and 32.9 which was due to the non-linear release of 3003-10 32.9 µm 50% whereby a large concentration of $KMnO_4$ was released between the 20 and 30 min sample time.

Equally the non-linear release of large concentrations (in comparison to linear release) was observed at 30 min time point for 3003-10 21µ 10% and 20% (FIG. 3). Particle size 15.6 µm hindered curing of any patch. The non-curing of particle size 11.9 µm 50% is likely due to the small size of particle and concentration of loading in comparison to the number of possible cross linking areas on the silicone backbone.

Release from Silicone 3003-20

Silicone 3003-20 release profiles are shown in FIGS. 4, 5, 6 and 7, demonstrating: i) linear release over 1 hr; ii) the greater the loading the greater the release; and iii) the smaller the particle the greater the release.

Again 50% loading of particle size 11.9 µm prevented curing, however the greatest release of 20% loading was from the particle size 11.9 µm. Error observed as standard deviation was variable with no known cause, however the sd deviation of 10% and 20%/across most release profiles was extremely low. Two exceptions were 3003-20 11.9µ 10% loading where greater variability was observed (FIG. 4) and 3003-20 15.6 µm 10% loading where large variability was observed. 3003-20 15.6 µm 20% and 50% did not cure and the large variability of the release of 10% loading may be due to very slight variations in the level of cure.

Release from Silicone 3003-30

FIGS. 8 through 11 show the release profiles of 3003-30. As for the other silicone types, the greater the loading the greater the release, all release profiles are linear and the smaller the particle the greater the release.

Of great note is the ability to cure 11.9 µm at 50% because the release profile at 30 min is greater (75 mM) than that of the intended concentration (66 mM). 3003-30 15.6 µm 20% and 50% did not cure and the release profile of 10% has a large sd. The difference between 3003-30 10% and 20% at 21 µm and 32.9 µm, respectively, are not significantly different.

Release from Silicone 3003-40

The cumulative release profiles of 3003-40 are shown in FIGS. 12-15 and hold similar trends to that of 3003-30: smaller the particle the greater release, increased loading gives rise to increased release and each profile is linear. The standard deviation is low across all profiles including 3003-40 15.6 µm 10%, however 20% and 50% did not cure.

Silicone Patch Shows Preferential Release to Treatment Areas

Advantageously, it has been found that the patches as disclosed herein comprising micro particulate potassium permanganate within a cured silicone matrix requires the presence of a liquid interface to release the permanganate.

Figure 12:
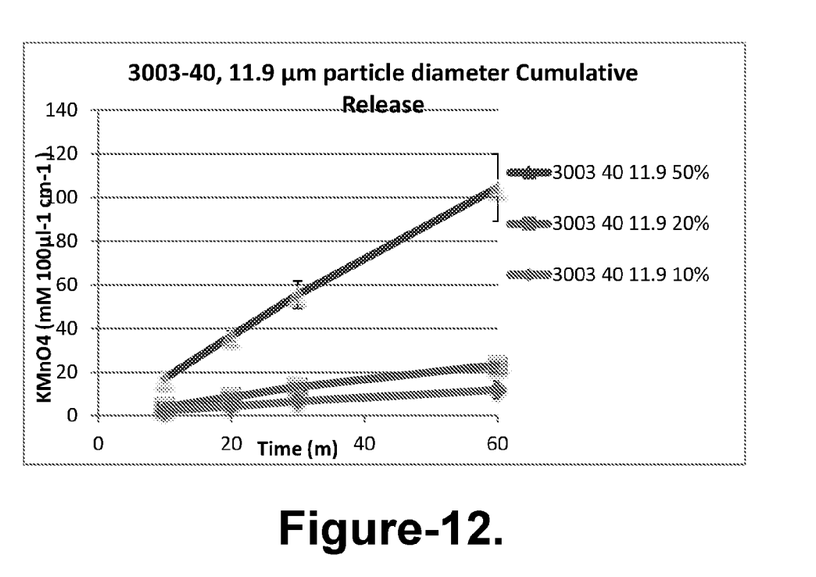
FIG. 12. The cumulative release of jet milled KMnO$_4$ particles having a diameter of 11.9 μm from silicone patches 3003-40 (shore hardness 40A) with 10%, 20% and 50% loading (N=3, ±SD)
Figure 13:
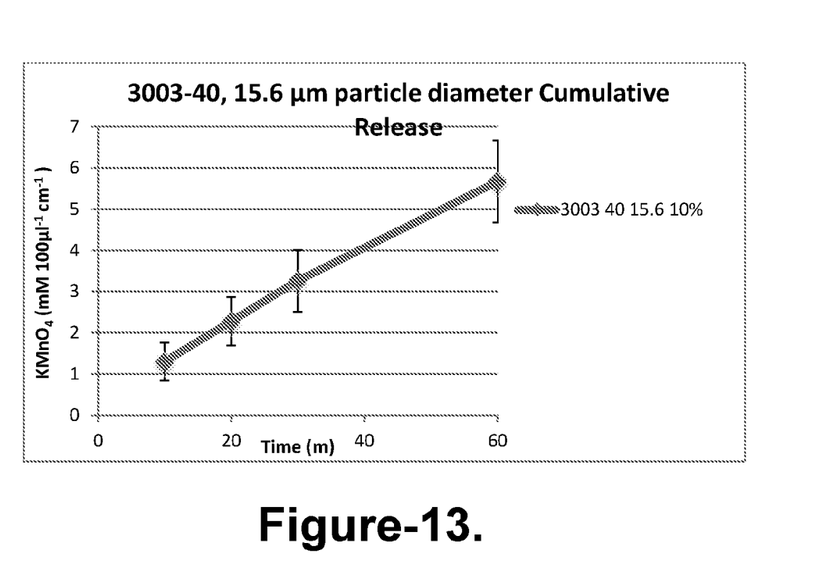
FIG. 13. The cumulative release of jet milled KMnO$_4$ particles having a diameter of 15.6 μm from silicone patches 3003-40 (shore hardness 40A) with 10% loading (N=3, ±SD). (note 3003 40 μm 20% 50% non-cure)
Figure 14:
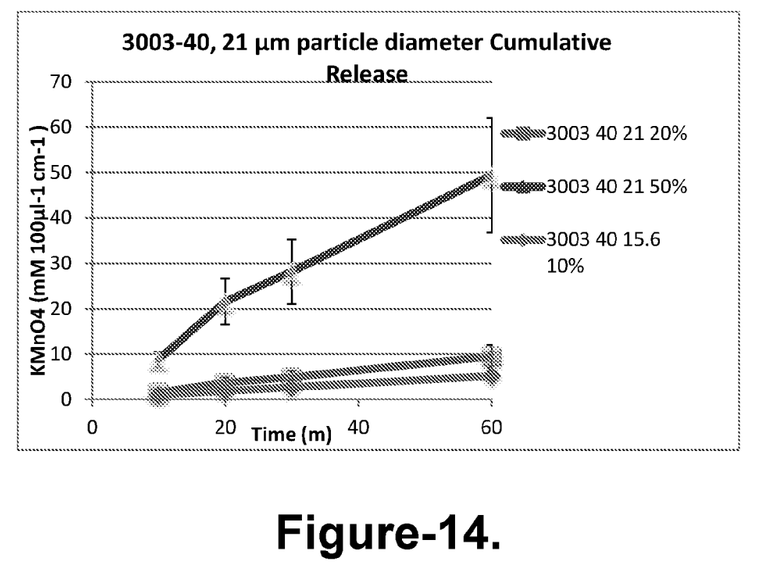
FIG. 14. The cumulative release of jet milled KMnO$_4$ particles having a diameter of 21 μm from silicone patches 3003-40 (shore hardness 40A) with 10%, 20% and 50% loading (N=3, ±SD)
Figure 15:
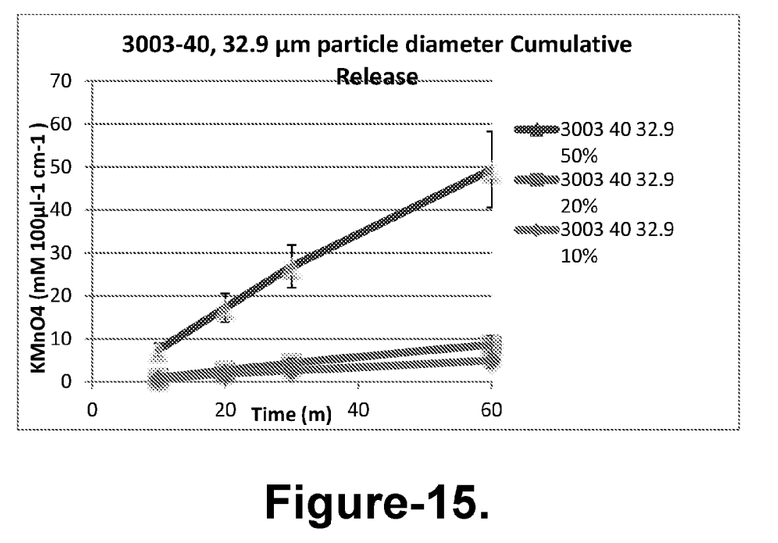
FIG. 15. The cumulative release of jet milled KMnO$_4$ particles having a diameter of 32.9 μm from silicone patches 3003-40 (shore hardness 40A) with 10%, 20% and 50% loading (N=3, ±SD)
Figure 16:
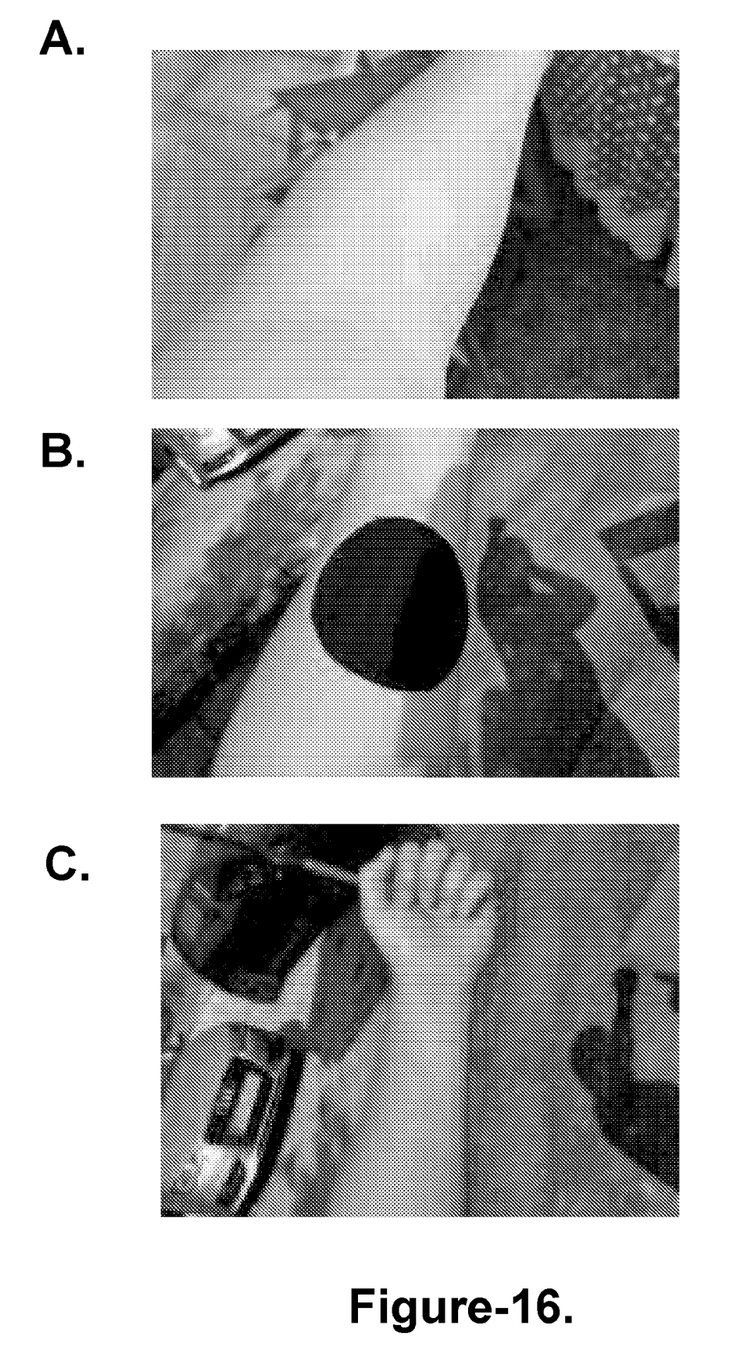
Figure 17:
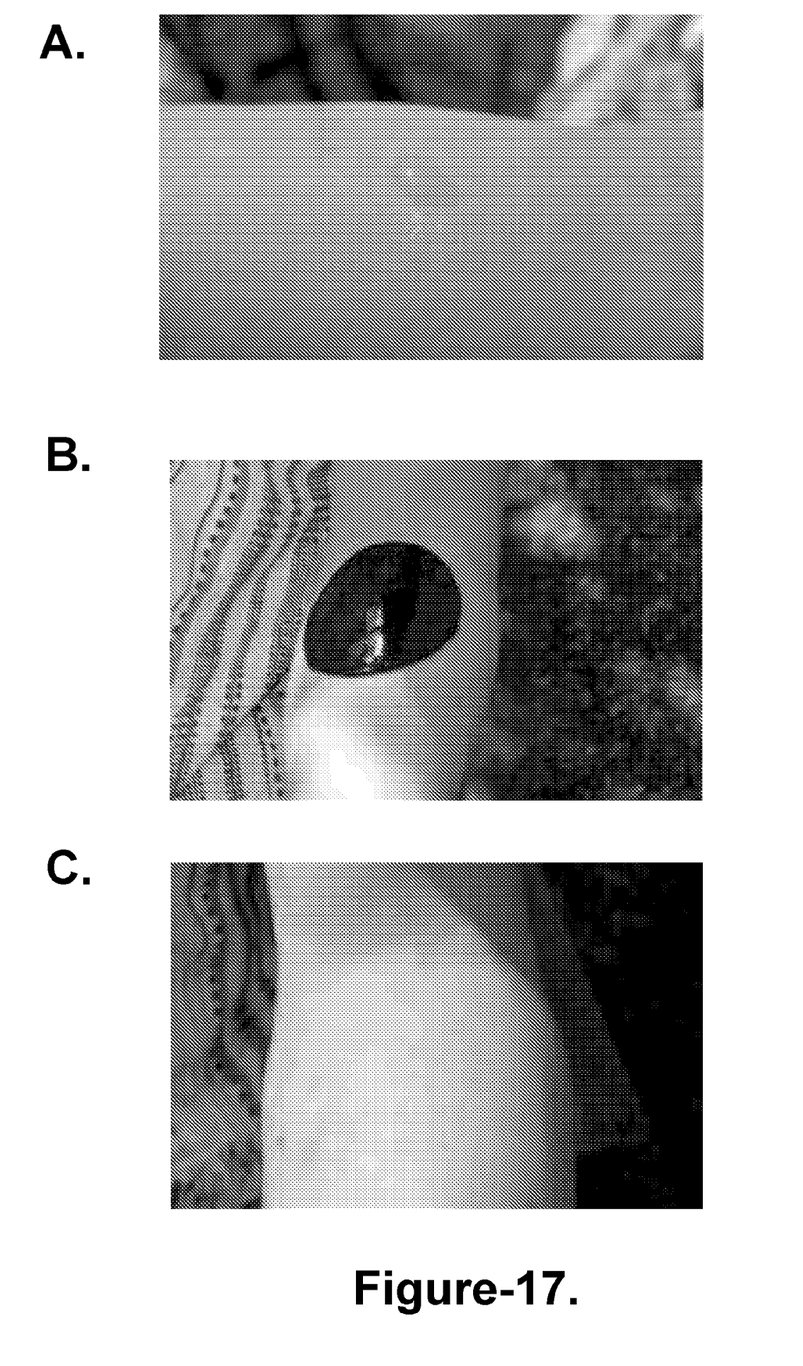

This is demonstrated in FIGS. 16 and 17. When a test patch was added to normal skin after 30 minutes there were no signs of permanganate release (permanganate release is evident when showing brown staining of the skin (FIG. 12*a-c*). When the skin was pre wetted (1 mL), however, and a patch applied it was observed that permanganate staining, and therefore release, has occurred (FIG. 13*a-c*)

The design and usage lends itself ideally to treatment for heavily exuding chronic wounds, whereby the practitioner places the patch for a period not exceeding 30 min on the wound. Although the patch is not specified to be used covering normal skin, the patch is designed so that normal skin humidity does not enable release of the permanganate, thereby avoiding release and risk of chemical burn. It therefore has an inherent safety mechanism that promotes handling and use.

Summary

Across all release profiles of increasing shore hardness medical grade 3003 silicone patches the smaller the particles of $KMnO_4$ the greater the concentration released. As shore hardness increased so did the ability to cure patches across at lower particle sizes, 15.6 µm prevented curing at all but two of the lowest concentrations and highest shore hardness (3003-30 and −40 at 10%).

Apart from two release profiles (3003-10 21 µm 20% and 3003-10 32.9µ 50%; FIGS. 2 and 3) all other profiles were linear over 1 hr.

In comparison of shore hardness and release (discounting 15.6 µm) the higher the shore hardness the lower the release, also the higher the shore hardness the lower the standard deviation between patches.

Our findings show that potassium permanganate, a chemical with advantageous wound healing properties but poor administration methods, can be delivered from a silicone matrix into a liquid in controlled and predictable manner according to the loading of the patch, the size of the particle and the shore hardness of the silicone used.

TABLE 1

| Silicone Shore Hardness | Particle size um | Percent loading (%) | Average Shore Hardness Post Loading (A) |
|---|---|---|---|
| 10A | 11.9 | 10 | 6.33 |
|  |  | 20 | 5.67 |
|  | 21 | 10 | 7.00 |
|  |  | 20 | 7.33 |
|  |  | 50 | 7.33 |
|  | 32.9 | 10 | 9.00 |
|  |  | 20 | 11.00 |
|  |  | 50 | 25.33 |
| 20A | 11.9 | 10 | 16.67 |
|  |  | 20 | 23.00 |
|  | 15.6 | 10 | 10.33 |
|  | 21 | 10 | 15.00 |
|  |  | 20 | 21.67 |
|  |  | 50 | 30.33 |
|  | 32.9 | 10 | 15.00 |
|  |  | 20 | 23.67 |
|  |  | 50 | 40.00 |
| 30A | 11.9 | 10 | 21.33 |
|  |  | 20 | 30.00 |
|  |  | 50 | 38.33 |
|  | 15.6 | 10 | 23.67 |
|  | 21 | 10 | 30.00 |
|  |  | 20 | 32.00 |
|  |  | 50 | 41.33 |
|  | 32.9 | 10 | 30.00 |
|  |  | 20 | 31.00 |
|  |  | 50 | 40.33 |
| 40A | 11.9 | 10 | 31.00 |
|  |  | 20 | 38.67 |
|  |  | 50 | 46.00 |
|  | 15.6 | 10 | 29.00 |
|  | 21 | 10 | 29.33 |
|  |  | 20 | 34.67 |
|  |  | 50 | 52.33 |
|  | 32.9 | 10 | 31.00 |
|  |  | 20 | 40.33 |
|  |  | 50 | 60.33 |

The invention claimed is:

1. A patch for applying to the skin of a subject, comprising medical grade silicone, wherein said silicone has a shore hardness between 5-60A and dispersed therein are potassium permanganate particles.

2. The patch according to claim 1 wherein said silicone has a shore hardness between 5-40A.

3. The patch according to claim 2 wherein said silicone has a shore hardness between 15-40A.

4. The patch according to claim 3 wherein said silicone has a shore hardness selected from the group consisting of: 15A, 16A, 17A, 18A, 19A, 20A, 21A, 22A, 23A, 24A, 25A, 26A, 27A, 28A, 29A, 30A, 31A, 32A, 33A, 34A, 35A, 36A, 37A, 38A, 39A, 40A and every 0.1A there between.

5. The patch according to claim 1 wherein said potassium permanganate particles are in the form of permanganate crystals dispersed throughout the silicone patch.

6. The patch according to claim 1 wherein said particles have an average diameter between 1 nm-60 μm.

7. The patch according to claim 6 wherein said particles have an average diameter between 1-50 μm.

8. The patch according to claim 7 wherein said particles have an average diameter selected from the group consisting of: 10 μm, 11 μm, 12 μm, 13 μm, 14 μm, 15 μm, 16 μm 17 μm, 18 μm, 19 μm, 20 μm, 21 μm, 22 μm, 23 μm, 24 μm, 25 μm 26 μm, 27 μm, 28 μm, 29 μm, 30 μm, 31 μm, 32 μm, 33 μm, 34 μm, 35 μm, and every 0.1 μm there between.

9. The patch according to claim 1 wherein said potassium permanganate is present in an amount between 5-75% by weight of the silicone patch and every 1% there between.

10. The patch according to claim 9 wherein said permanganate is present in an amount between 10-50% by weight of the silicone patch and every 1% there between.

11. The patch according to claim 10 wherein said permanganate is present in an amount selected from the group consisting of: 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, and every 0.1% there between.

12. The patch according to claim 1 wherein said silicone has a shore hardness of about 20A, said potassium permanganate dispersed therein is of a particle size of about 12 μM and at a concentration of about 20% by weight of said patch.

13. The patch according to claim 1 wherein said silicone has a shore hardness of an amount about 30A, said potassium permanganate dispersed therein is of a particle size of about 20 μm and at a concentration of about 50% by weight of said patch.

14. The patch according to claim 1 wherein said silicone has a shore hardness of an amount about 40A, said potassium permanganate dispersed therein is of a particle size of about 33 μm and at a concentration of about 50% by weight of said patch.

15. The patch according to claim 1 wherein said silicone has a shore hardness of an amount about 25A, said potassium permanganate dispersed therein is of a particle size of about 33 μm and at a concentration of about 50% by weight of said patch.

16. The patch according to claim 1 wherein said silicone has a shore hardness of an amount about 38A, said potassium permanganate dispersed therein is of a particle size of about 12 μm and at a concentration of about 50% by weight of said patch.

17. A method for treating a skin disorder characterized by increased skin surface moisture, said method comprising the step of applying the patch according to claim 1 to the surface of the skin to be treated whereupon contact with said skin surface moisture, potassium permanganate is released from the patch.

18. The method according to claim 17 wherein said skin disorder is selected from the group comprising-consisting of: wounds; acute wounds; incisions; lacerations; abrasions; avulsions; punctures; thermal or chemical burns; bites and stings; ulcers; eczema; viral, fungal, or bacterial skin infections; acne; bowens disease; squamous cell carcinoma; contact dermatitis; Dystrophic epidermolysis bullosa; fungal infections of nails; herpes simplex; psoriasis; Pyoderma gangrenosum; and shingles.

19. The patch according to claim 1 wherein the potassium permanganate particles are releasably contained in the patch.

20. The patch according to claim 1 wherein the potassium permanganate particles release from the patch upon contact with skin surface moisture.

* * * * *